(12) United States Patent
Kuhar et al.

(10) Patent No.: US 6,358,492 B1
(45) Date of Patent: *Mar. 19, 2002

(54) DOPAMINE TRANSPORTER IMAGING LIGAND

(75) Inventors: Michael J. Kuhar, Baltimore, MD (US); Frank I. Carroll, Durham, NC (US); John W. Boja, Cuyahoga Falls, OH (US); Anita H. Lewin, Chapel Hill; Philip Abraham, Cary, both of NC (US)

(73) Assignee: Research Triangle Institute, Research Triangle Park, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/946,007

(22) Filed: Oct. 7, 1997

(51) Int. Cl.[7] .................. C07D 451/02; A61K 31/304; A61K 51/00

(52) U.S. Cl. ...................... 424/1.85; 546/132

(58) Field of Search ........................ 546/132; 424/185

(56) References Cited

U.S. PATENT DOCUMENTS 5,413,779 A * 5/1995 Kuhar et al. ............... 424/1.85
5,439,666 A * 8/1995 Neumeyer et al. ......... 424/1.85

FOREIGN PATENT DOCUMENTS

WO   WO 94/04146   3/1994

OTHER PUBLICATIONS

Christopher R. Holmquist et al., *3α–(4′–Substituted phenyl)Tropane–2β–carboxylic Acid Methyl Esters: Novel Ligands with High Affinity and Selectivity at the Dopamine Transporter*, J. Med. Chem., 1996, vol. 39, pp. 4139–4141, XP002914107.

Kathryn I. Keverline et al., *Synthesis of the 2β,3α–and 2β,3β–Isomers of 3–(p–lSubstitue Phenyl)Tropane–2–Carboxylic Acid Methyl Esters*, Tetrahedron Letters, vol. 36, No. 18, pp. 3099–3102, 1995, XP004028199.

Kjell Nagren et al., *Comparison of –[11C] Methyl Triflate and [11C]Methyl Iodide in the Synthesis of PET Radioligands such as [$^{11}$C]β–CIT and [$^{11}$C]β–CFT*, Nucl. Med. Biol., vol. 22, No. 8, pp. 965–970 1995, XP004051699.

* cited by examiner

*Primary Examiner*—Alan L. Rotman
(74) *Attorney, Agent, or Firm*—Oblon, Spivak, McClelland, Maier & Neustadt, P.C.

(57) ABSTRACT

The 3α isomer of RTI-55, RTI-352, is an effective in vivo binding ligand that reflects greater selectivity for the dopamine transporter than is observed with RTI-55. In addition, there is also a more rapid achievement of apparent equilibrium in the striatal-to-cerebellar ratio (compared to RTI-55) as the ratio peaks at about 30 min and is maintained for about 20 min thereafter. Such apparent equilibrium is useful in developing an approach to measuring the number of dopamine transporters present in tissues. Moreover, these results indicate that the utilization of 3α isomers of a variety of 3β-(substituted phenyl)tropanes will result in greater selectivity for dopamine transporters and a more rapid of achievement of apparent equilibrium.

3 Claims, 2 Drawing Sheets

DOPAMINE TRANSPORTER IMAGING LIGAND

BACKGROUND OF THE INVENTION

1. Field of the Invention

The present invention is directed to novel dopamine transporter imaging ligands that exhibit high selectivity for dopamine transport combined with a rapid apparent equilibrium of striatal-to-cerebellar ratios.

2. Discussion of the Related Art

Since the initial preparation by Clarke and co-workers over twenty-three years ago, (Clarke et al, J. Med. Chem., 16, 1260-1267 1973), the 3β-(substituted phenyl)tropane-2β-carboxylic acid methyl ester class of compounds has been widely employed in structure-activity relationship (SAR) studies at the cocaine binding site on the dopamine transporter (DAT).

The 3β (substituted phenyl)tropane-2β-carboxylic acid esters are effective in vivo binding ligands for dopamine transporters (DATS) (Scheffel and Kuhar, Synapse 4:390–392, 1989; Boja et al., Dopamine Receptors & Transporters, 611–694, Marcel Dekker, Inc., 1994). For example, RTI-55, a member of this class, has been used in many studies in animals and humans as a Positron Emission Tomography (PET) or SPECT (single photon emission computed tomography) ligand (Boja et al., Ann. N.Y. Acad. of Sci. 654:282–291, 1992, and Boja et al., 1994). Highly desirable properties of a DAT ligand include rapid penetration into the brain, achievement of rapid apparent equilibrium, and high signal to noise ratios. Various 3β-phenyltropane analogs and other compounds possess these properties to varying degrees.

SUMMARY OF THE INVENTION

The 3α isomer of RTI-55, RTI-352, is an effective in vivo binding ligand that reflects greater selectivity for the dopamine transporter than is observed with RTI-55. In addition, there is also a more rapid achievement of apparent equilibrium in the striatal-to-cerebellar ratio (compared to RTI-55) as the ratio peaks at about 30 min and is maintained for about 20 min thereafter. Such apparent equilibrium is useful in developing an approach to measuring the number of dopamine transporters present in tissues. Moreover, these results indicate that the utilization of 3α isomers of a variety of 3β-(substituted phenyl)tropanes will result in greater selectivity for dopamine transporters and a more rapid achievement of apparent equilibrium.

(B) denotes tissue-to-cerebellar ratios of [$^3$H] activity after i.v. injection of [$^3$H]RTI-352.

CEREB.—cerebellum; HYP. hypothalamus; CTX.= parietal cortex; OLF.T.=olfactory tubercles; STR.=striatum.

Data are presented as means±s.e.m.; n=4–8.

Figure 1A:
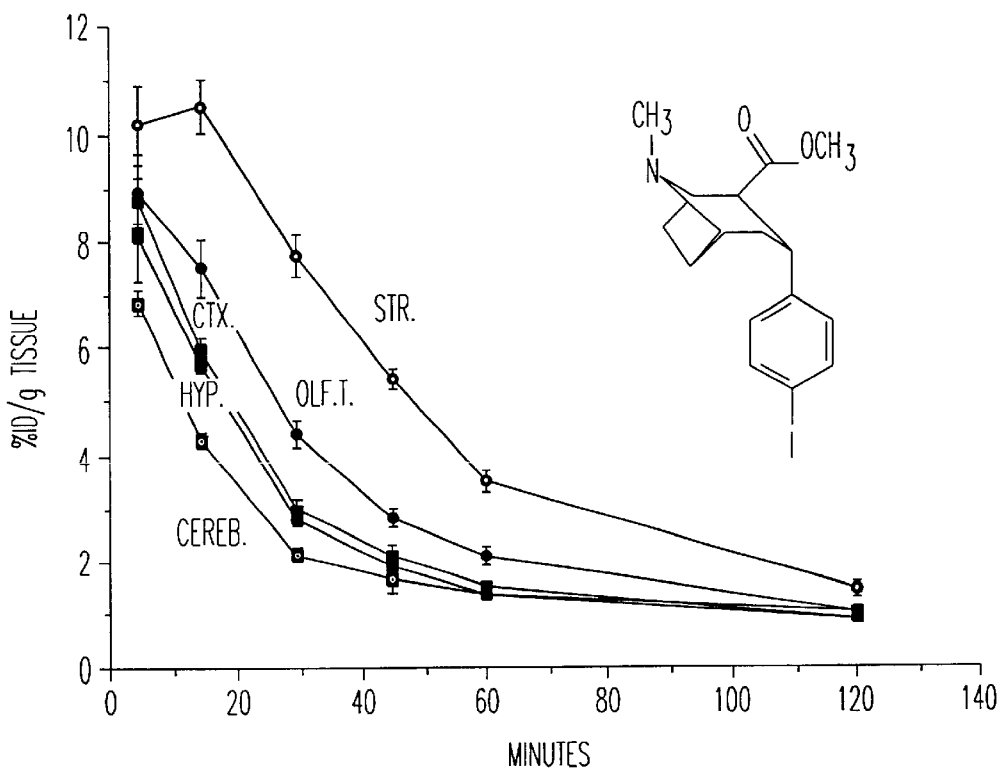
In FIG. 1, (A) denotes time course of tritium concentrations in five regions of the mouse brain after i.v. injection of 1 μCi of [$^3$H]RTI-352. Inset shows structure of RTI-352.
Figure 1B:
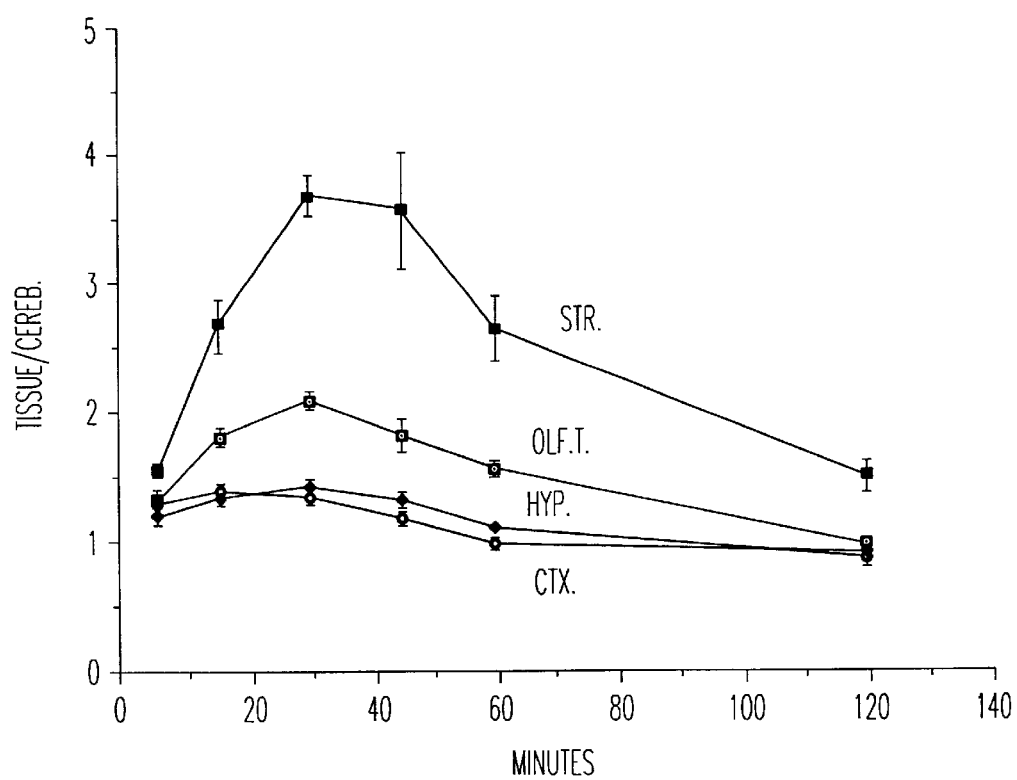
Figure 2A:
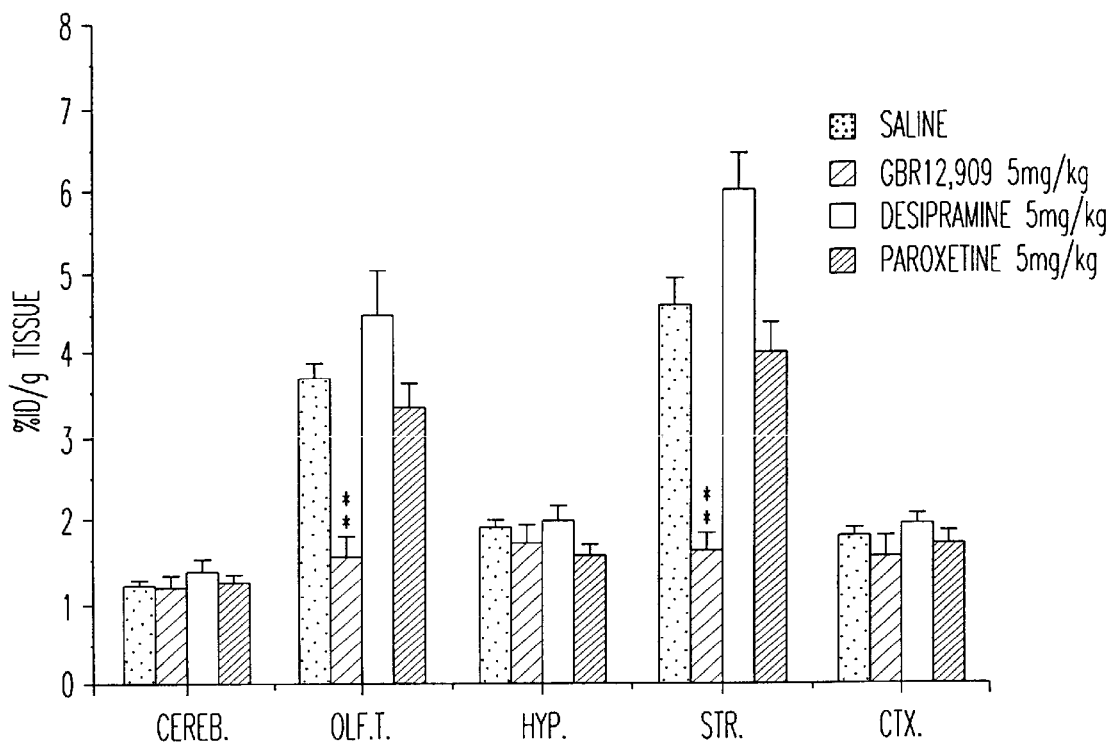
Figure 2B:
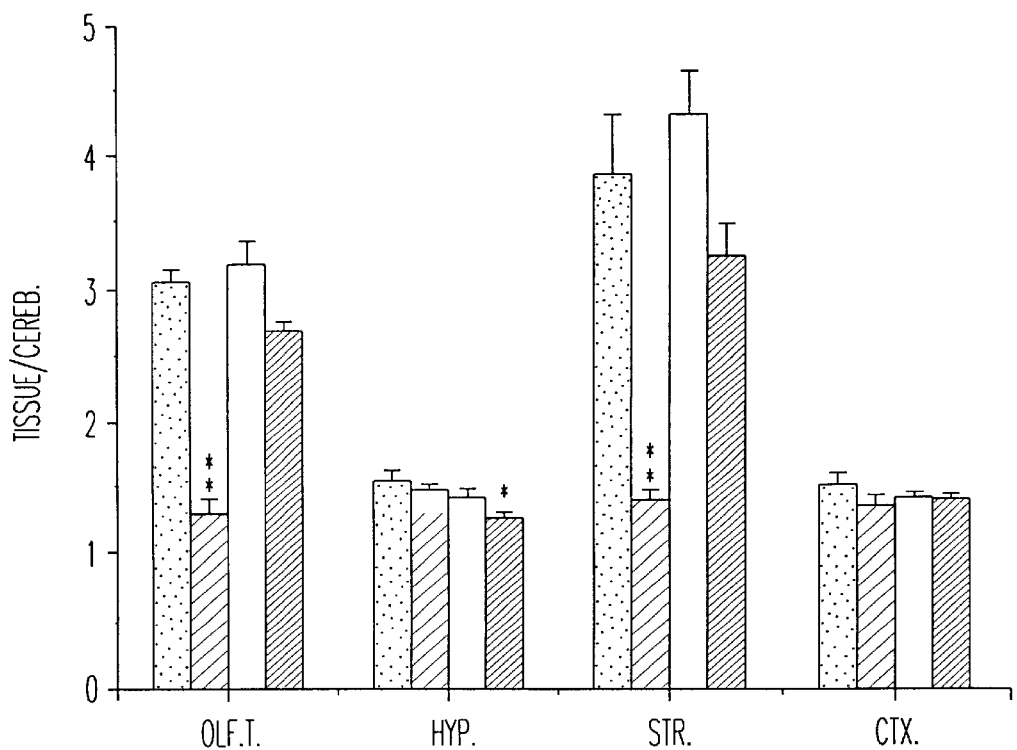

In FIG. 2, (A) denotes tissue concentrations of [$^3$H]RTI-352 in five regions of mouse brain with and without pretreatment of the animals with blocking doses of 5 mg/kg GBR12,909, a selective inhibitor of the DAT, desipramine, a selective ligand for the NET, and paroxetine, a selective ligand for the 5-HT-transporter (SERTs). The blocking doses were injected intravenously at 5 minutes before i.v. administration of [$^3$H]RTI-352. The mice were sacrificed thirty minutes after tracer injection. Abbreviations same as in FIG. 1.

Data are expressed as means±s.e.m., n=4–5. in each group. Significant difference from control: *p<0.05 **p<00.1.

(B) denotes tissue to cerebellar radioactivity ratios 30 minutes after i.v. injection of [$^3$H]RTI-352. Experimental details and data presentation same as in FIG. 2A.

DESCRIPTION OF THE PREFERRED EMBODIMENTS

Applicants have recently found that the 3α isomers of several 3β (substituted phenyl)tropanes exhibit only slight reduction in affinity for DATs but have a larger reduction in affinity at serotonin transporters. This suggests that these isomers would still be effective as DAT ligands, but exhibit greater selectivity because of reduced affinity at SERTs. Indeed, the 3α isomer (RTI-352) of RTI-55, which has a high affinity for SERTs shows much lower affinity for SERTs than RTI-55 (Scheffel et al., Synapse 11:134–139, 1992) (Holmquist et al., submitted 1996). Applicants have studied the in vivo binding of DAT by radiolabeled RTI-55, and have found greater selectivity by RTI-352 for DAT, but also, quite unexpected achievement of a more rapid apparent equilibration of striatal-to-cerebellar ratios.

Male CD mice weighting 25–35 g received 1 μCi [$^3$H] RTI-352 (52 mg, diluted in saline containing 0.5% methanol) by intravenous injection. The animals were killed at different times, and [$^3$H]RTI-352 concentrations in different brain regions determined as previously described (Scheffel et al., 1989; Cline et al., 1992). To evaluate the selectivity of [$^3$H]RTI-352 in vivo binding, blocking doses (5 mg/kg, dissolved in 0.1 ml saline) of GBR 12,909 (DAT blocker), desipramine (NET blocker), or paroxetine (5-HTT blocker) were injected intravenously 5 minutes before [$^3$H] RTI-352 tracer injection. The animals were killed 30 minutes later and [$^3$H]RTI-352 concentrations determined in the various brain tissues.

The penetration into brain was very rapid and the efflux from brain was also relatively rapid (FIG. 1). The percent dose per gram tissue peaked rapidly in all regions of the brain and was maintained for a slightly longer time in the striatum compared to other tissues that lack DAT. The tissue to cerebellar ratios reflected this fact in that striatal to cerebellar ratios were relatively high at early times but low at later times (FIG. 1). In parallel experiments, in vivo labeling of [$^{125}$I]RTI-55 was studied and the previously noted slow approach to equilibrium (striatal to cerebellar ratios were steadily increasing at 120 min.) was found (Cline et al., Synapse 12:27–36 1992). The hypothalamus, which contains high densities of serotonin transporters, showed only little enrichment of [$^3$H]RTI-352 binding at any time (hypothalamus/cerebellum ratio of 1.4 shown). This is in contrast to what was observed for [$^{125}$I]RTI-55 where there was a relatively longer lasting accumulation of radioactivity in this region because of its binding to serotonin transporters.

These findings indicate that the 3α isomer of RTI-55, RTI-352, is an effective in vivo binding ligand that reflects greater selectivity than was observed with RTI-55 (Holmquist et al., 1996). However, there was also a more rapid achievement of apparent equilibrium in the striatal-to-cerebellar ratio (compared to RTI-55) as the ratio peaked at about 30 min and was maintained for about 20 min thereafter. Such apparent equilibrium might be useful in developing an approach to measuring the number of dopamine transporters present in tissues. Moreover, these results suggest that the utilization of 3α-isomers of a variety of 3β-(substituted phenyl)tropanes will result in greater selectivity for dopamine transporters and a more rapid achievement of apparent equilibrium. This also indicates that of physiological evaluation of dopamine uptake/binding event may be selectively addressed by administration of these compounds.

Since neither Clarke's nor any other reported method provided the 3α-phenyl analogs, the SAR studies did not include this isomer. Recently, we reported the synthesis of the first 3α-(substituted phenyl)tropane-2β-carboxylic acid methyl esters by samarium iodide reduction of 3-aryl-2-carbomethoxytropenes. (Keverline et al, Tetrahedron Letters, 36:3099–3102 1995).

The route used to synthesize the 3α-(substituted phenyl) tropane-2β-carboxylic acid methyl ester (2a–e) analogs is shown in Scheme 1, and the physical properties are listed in Table 1. Addition of a solution of (1R,5S)-2-(3'-methyl-1', 2',4'-oxadiazol-5'-yl)-8-methyl-8-azabicyclo[3.2.1]oct-2-ene (4) in anhydrous tetrahydrofuran or ether to a −78° C. solution of the appropriate aryl lithium followed by quenching with trifluoroacetic acid at −78° C. formed 3α (substituted phenyl)tropane-2α-(3'-methyl-1',2',4'-oxadiazol-5'-yl)tropanes (5). In some cases (X=$CH_3$, I) the 2α,3β-isomer was also formed; this isomer could either be removed by flash column chromatography or carried through the next reaction and separated at the next stage.

Conversion of the oxadiazole to the methyl ester was accomplished by reduction with nickel boride and hydrochloric acid in refluxing methanol. Under the reaction conditions, complete epimerization at C-2 to form the 2β,3α stereoisomer is observed. This is in agreement with previously reported observations on 3αa-phenyl-2α-(3'-methyl-1',2',4'-oxadiazol-5'yl)tropane (5e, X=H), F. I. Carroll et al., J. Med. Chem. 36:2888–2890 (1993) and is presumably driven by the ability of the piperidine ring of the tropane moiety to adopt an equatorially substituted twist boat conformation (Scheme 2).

Analysis of the $^1$H and COSY spectra of methyl esters 2a–e (Table 2), using pyridine-$d_5$ as solvent for chemical shift dispersion, shows small coupling between $H_1$ and $H_2$ ($J_{1,2}$=~1.7) while $H_2$ couples to $H_3$ with a coupling constant of 9.4–9.7 Hz. These observations are consistent with a twist boat conformation in which $H_2$ is close to orthogonal with $H_1$ and has a near trans-diaxial relationship to $H_3$. This contrasts sharply with allococaine structure (6), where the $^1$H NMR and $^{13}$C NMR data show that this compound possesses a chair conformation. As in the 2β,3β-isomers 1, the equatorial proton at C-4 of the 2β,3α-isomers 2 is deshielded relative to its axial counterpart, indicating that the aromatic ring lies perpendicular to the axis of the piperidine ring.

The $IC_{50}$ values for the inhibition of ligand binding to the dopamine, serotonin, and norepinephrine transporters by 3α-(p-substituted phenyl)tropane-2β-carboxylic acid methyl esters 2a–e are listed in Table 3. For comparison, the previously reported $IC_{50}$ values for the corresponding 2β,3β-isomers 1a–e, as well as values for cocaine (7) and allococaine (6), are also listed. The $IC_{50}$ values for dopamine and serotonin represent inhibition of 0.5 nM [$^3$H]WIN 35,428 and 0.2 nM[$^3$H] paroxetine respectively as previously described. Norepinephrine $IC_{50}$ values represent inhibition of 0.5 nM [$^3$H] nisoxetine binding to the norepinephrine transporter.

The substituted aryl 2β,3α-isomers 2a–d are more selective for the DAT relative to the 5-HT transporter than the 2β,3β-isomers 1a–d. The unsubstituted analog 2e possessed DAT selectivity similar to WIN 35,065-2. Furthermore, the 2β,3α-isomers are only 1.5 to 5.9-times less potent at the DAT than the analogous 2β,3β-isomers. These results contrast sharply with allococaine, the 2β,3α-stereoisomer of cocaine, which is 60-times less potent than cocaine at the DAT. Apparently, the preference of 2β,3α esters 2 for the twist boat conformation allows the amino, aryl, and carbomethoxy groups to adopt similar positions to the corresponding groups in 1 and may explain the relatively high dopamine binding affinities exhibited by esters 2 relative to allococaine 6. It is interesting to note that the p-iodophenyl analog 2b (RTI-352) is only slightly less potent than 1b (RTI-55) but is 7-times more selective for the DAT relative to the 5-HT transporter. Since [$^{123}$I]RTI-55 has proven to be a valuable SPECT (single photon emission computed tomography) imaging agent, we plan to conduct further studies with 2b to determine if it possesses properties that would make it a better SPECT imaging agent than [$^{123}$I] RTI-55.

EXAMPLES

3α-(4-Fluorophenyl)-2β-(3'-methyl-1',2',4'-oxadiazol-5'-yl)tropane (5a)

A 250 mL r.b. flask was equipped with a stirbar, thermometer with adapter and an addition funnel with nitrogen inlet. The assembly was flame-dried and allowed to cool under nitrogen. The flask was charged with a solution of bromofluorobenzene (4.2 g, 24 mmol) in 45 mL of dry THF and cooled to −78° C. in an dry ice/acetone bath. t-Butyllithium (1.7M in pentane, 48 mmol, 28.3 mL) was added dropwise, maintaining the temperature below −55°C. After 20 min at −78° C., a solution of anhydroecgonine oxadiazole 4(2.1 g, 10 mmol) in 10 mL of anhydrous THF was added dropwise. The reaction was stirred at −78° C. for 2 h, then quenched at −78°C. by dropwise addition of a 20% solution of trifluoroacetic acid in ethyl ether (5 mL). The reaction was allowed to warm to room temperature and concentrated. The residual oil was purified by flash column chromatography (3:1 ethyl acetate/petroleum ether+5% saturated ammonia in methanol) to give compound 5a as a colorless oil which solidified on standing. Yield: 2.55 g (85%); mp 71–72° C.; $[\alpha]D^{25}$=−78.4° (c 0.32, $CHCl_3$); $^1$H NMR ($CDCl_3$) δ7.12 (m, 2H), 6.91 (m, 2H), 3.32–3.48 (m, 3H), 3.65 (m, 1H), 3.01 (dd, 1H), 2.51 (m, 1H) 2.32 (s, 3H), 2.26 (s, 3H), 2.14–2.28 (m, 1H), 1.54–1.70 (m, 2H), 1.37 (m, 1H); $^{13}$C NMR ($CDCl_3$) δ181.77, 166.98, 161,46 (d), 138.60, 129.16, 129.04, 115.43, 115.09, 64.26, 59.36, 50.00, 41.05, 39.61, 37.54, 29.11, 11.60; Analysis calculated for $C_{17}H_{20}N_3OF$: C, 67.74;H, 6.70; N, 13.94. Found: C, 67.76;H, 6.71; N, 13.86.

3α-(4-Fluorophenyl)tropane-2β-carboxylic acid methyl ester (2a)

A 250 mL r.b. flask equipped with a stirbar and a condenser was charged with nickel(II) acetate (5.3 g, 21.4 mmol) and methanol (50 mL). A solution of sodium borohydride (0.8 g, 21.4 mmol) in methanol (25 mL) was added dropwise resulting in an exothermic reaction. A black colloidal suspension formed immediately. A solution of 5a (1.3 g, 4.3 mmol) in 50 mL of methanol and 1.8 mL of concentrated HCl was slowly added and the resulting mixture stirred for 2 h at room temperature then heated at reflux for 3 h. The reaction was allowed to cool to room temperature then ethyl ether (100 mL) and saturated bicarbonate were added. The pH of the solution was adjusted to 10–11 by careful addition of concentrated ammonium hydroxide. Following extraction with ethyl ether (4×20 mL), the organic phase was washed with water (3×20 mL), dried over sodium sulfate, filtered and concentrated under vacuum. Compound 2a was isolated as a colorless oil which was converted to the D-tartrate salt. Yield: 1.0 g (86%). mp 65° C. (dec); $[\alpha]_D^{25}$= 34.4° (c 0.54, methanol) ; 1H NMR (CD$_3$OD) δ7.42 (m, 2H), 7.07(m, 2H), 4.12 (m, 1H), 3.93 (m, 1H), 3.66 (s, 3H), 3.40–3.23 (m, 2H), 2.80 (s, 3H), 2.68–2.55 (m, 1H), 2.39 (m, 2H), 2.16–1.98 (m, 3H); Analysis calculated for $C_{20}H_{26}FNO_8$-0.5 H$_2$O: C, 55.04; H, 6.24; N, 3.21. Found: C, 55.09, H, 6.28; N, 3.16.

3α-(4-Iodophenyl)-2β-(3'-methyl-1',2',4'-oxadiazol-5'-yl)tropane tosylate (5b)

A 1 L two-necked flask was equipped with a stirbar, thermometer with adapter and an addition funnel with nitrogen inlet. The assembly was flame-dried and allowed to cool under nitrogen. The flask was charged with a solution of 1,4-diiodobenzene (20.70 g, 63 mmol) in 350 mL of anhydrous THF and cooled to −65° C. in an dry ice/acetone bath. Diiodobenzene precipitated out of solution. t-Butyllithium (1.7 M in pentane, 126 mmol, 74 mL) was added dropwise over 30 min, maintaining the temperature below −55° C. The resulting dark green solution was cooled to −78° C. The addition funnel was rinsed with 10 mL of anhydrous THF, then charged with a solution of anhydroecgonine oxadiazole (4, 6.15 g, 30.0 mmol) in 25 mL of anhydrous THF. This solution was added to the reaction dropwise, maintaining the temperature below −70° C. The resulting brown solution was stirred at −78° C. for 2.5 h, then quenched at −78° C. by dropwise addition of a 20% solution of trifluoroacetic acid in ethyl ether (50 mL). The reaction was allowed to warm to room temperature, then successively washed with saturated sodium bicarbonate (25 mL) and 1 N HCl (4×25 mL). The aqueous phase was washed with ethyl ether (1×50 mL) and the ethereal layers discarded. The aqueous layer was neutralized to pH 10 by addition of concentrated ammonium hydroxide then extracted with dichloromethane (4×50 mL).

The organic phase was dried over sodium sulfate, filtered and concentrated under vacuum. The residual oil was purified by flash column chromatography (3:1 ethyl acetate/petroleum ether together with 5% saturated ammonia in methanol) to give 5b as a colorless oil which solidified on standing. Also recovered from the crude product was 2.06 g (20%) of the 2α,3β-isomer. Compound 5b was converted to the tosylate salt for characterization. Yield: 2.61 g (23%); MP 208.2–109.8° C.; $[\alpha]_D^{25}$ −60.52° (c 0.760, methanol) ; $^1$H NMR (CDCl$_3$) δ11.18 (br s, 1H), 7.76 (d, 2H, J=8.2 Hz), 7.59 (d, 2H, J=8.4 Hz), 7.17 (d, 2H, J=8.1 Hz), 6.91 (d, 2H, J 8.5 Hz), 4.28 (d, 1H, J=6.6 Hz), 4.18 (t, 1H, J=6.2 Hz), 3.87–3.79 (m, 1H), 3.53 (d, 1H, J 8.0 Hz), 3.12–3.01 (m, 1H), 2.94 (s, 3H), 2.58–2.50 (m, 1H), 2.37 (s, 3H), 2.30 (s, 3H), 2.26–2.14 (m, 1H), 2.12–2.00 (m, 1H), 1.91–1.81 (m, 2H); $^{13}$C NMR (CDCl$_3$) δ177.36, 167.16, 142.51, 139.87, 139.80, 137.71, 129.25, 128.71, 125.86, 92.78, 64.00, 61,59, 46.29, 39.68, 35.83, 34.81, 27.02, 26.32, 21.29, 11.42; Analysis calculated for $C_{24}H_{28}IN_3O_4S$: C, 49.57; H, 4.85; N, 7.23. Found: C, 49.50; H, 4.84; N, 7.13.

3α-(4-Iodophenyl)tropane-2β-carboxylic acid methyl ester tosylate (2b):

A 250 mL r.b. flask equipped with a stirbar and a condenser was charged with nickel(II) acetate (9.0 g, 36.0 mmol) and methanol (50 mL). A solution of sodium borohydride (1.4 g, 36.0 mmol) in methanol (15 mL) was added dropwise resulting in an exothermic reaction. A black colloidal suspension formed immediately. A solution of 5b (4.9 g, 12.0 mmol) in 25 mL of methanol and 3.0 mL of concentrated HCl was added and the resulting mixture heated at reflux for 4 h. The reaction was allowed to cool to room temperature then filtered through celite. The pale green filtrate was concentrated to approximately 15 mL and diluted with water (50 mL). The pH of the solution was adjusted to 10–11 by careful addition of concentrated ammonium hydroxide. Following extraction with ethyl ether (4×20 mL), the organic phase was washed with water (3×20 mL), dried over sodium sulfate, filtered and concentrated under vacuum. The residual oil was purified by flash column chromatography (5:3 petroleum ether/ethyl acetate together with 2% methanolic ammonia) gave pure 2b as a colorless oil. Yield: 2.1 g (45%). This material was converted to the tosylate salt for characterization. mp 204.6°–205.3° C.; $[\alpha]D^{25}$ −38.91° c 1.30, methanol) ; $^1$H NMR (CD$_3$OD) 87.74–7.65 (m, 4H), 7.27–715 (m, 4H), 4.15 (d, 1H, J=6.8 Hz), 3.76 (t, 1H, J=6.4 Hz), 3.68 (s, 3H), 3.38–3.25 (m, 2H), 2.82 (s, 3H), 2.62–2.47 (m, 1H), 2.43–2.20 (m, 6H), 2.06–1.92 (m, 2H) ; $^{13}$C NMR (CD$_3$OD) δ174.70, 142.43, 142.36, 141.75, 138.99, 130.44, 129,89, 127.0, 91.24, 64,.87; 63,43, 53,25, 52.83, 39.69, 35.53, 35.14, 26.01, 25.98, 21.36; Analysis calculated for $C_{23}H_{28}INO_5S$: C, 49.55; H, 5.30; N, 2.5. Found: C, 49.47; H, 5.05; N, 2.53.

3α-(4-Chlorophenyl)-2β-(3'-methyl-1',2',4'-oxadiazol-5'-yl)tropane tosylate (5c)

A 250 m-L three-neck flask was equipped with a stirbar, septum, thermometer with adapter and an addition funnel with nitrogen inlet. The assembly was flame-dried and allowed to cool under nitrogen. The flask was charged with a solution of 1-chloro-4-iodobenzene (6.55 g, 27.5 mmol) in 50 mL of anhydrous ethyl ether and cooled to 0° C. t-butyllithium (1.7M in pentane, 55 mmol, 32.3 mL) was added dropwise over 15 min. The resulting yellow solution was stirred for 20 min, then cooled to −78° C. in a dry ice/acetone bath. The addition funnel was rinsed with 5 mL of anhydrous ether, then charged with a solution of anhydroecgonine oxadiazole (4, 2.56 g, 12.5 mmol) in 20 mL of anhydrous ethyl ether. This solution was added to the reaction dropwise, maintaining the temperature below −70° C. A mild exotherm was observed during the addition. The resulting brown solution was stirred at −78° C. for 2.5 h then quenched at −78° C. by dropwise addition of a 20% solution of trifluoroacetic acid in ethyl ether (25 mL). The reaction was allowed to warm to room temperature, then successively washed with saturated sodium bicarbonate (15 mL) and 1N HCl (2×25 mL). The aqueous phase was washed with ethyl ether (1×25 mL) and the ethereal layers discarded. The aqueous layer was neutralized to pH 10 by addition of concentrated ammonium hydroxide then extracted with dichloromethane (3×50 mL). The organic phase was dried over sodium sulfate, filtered and concentrated under vacuum. The residual oil was purified by flash column chromatography (3:1 ethyl acetate/petroleum ether together with 5% saturated ammonia in methanol) to give 3.20 g (81%) of 5c as a colorless oil. This compound was converted to the tosylate salt for characterization: mp 174.9–178.2° C.; $[\alpha]_D^{25}$ =7.56° c 0.515, methanol); $^1$H NMR (CD$_3$OD) δ7.70 (d, 2H, J=8.2 Hz), 7.39 (d, 2H, J=8.7 Hz), 7.34 (d, 2H, J=8.9 Hz), 7.22 (d, 2H, j=8.0 Hz), 4.31 (d, 1H, J=6.5 Hz), 4.10–3.98 (m, 2H), 3.45 (q, 1H, J=8.13 Hz), 2.87 (s, 3H), 2.72–2.54 (m, 2H), 2.51–2.45 (m, 2H), 2.36 (s, 3H), 2.25 (s, 3H, 2.23–2.05 (m, 2H); Analysis calculated for $C_{23}H_{28}ClN_3O_4S$: C, 57.78; H, 5.90; N, 8.79. Found: C, 58.22, H, 5.76; N, 8.42.

3α-(4-Chlorophenyl)tropane-2β-carboxylic acid methyl ester tosylate (2c)

A 50 mL r.b. flask equipped with a stirbar and a condenser was charged with nickel (II) acetate (0.89 g, 3.6 mmol) and methanol (10 mL). A solution of sodium borohydride (0.14 g, 3.6 mmol) in methanol (3 mL) was added dropwise resulting in an exothermic reaction. A black colloidal suspension formed immediately. A solution of 5c (0.57 g, 1.80 mmol) in 5 mL of methanol and 0.33 mL of concentrated HCl was added and the resulting mixture heated at reflux for 4 h. The reaction was allowed to cool to room temperature then filtered through celite. The celite was washed with methanol (50 mL) and the filtrate concentrated under vacuum. The residue was diluted with water (10 mL) and poured into ethyl ether (50 mL). The aqueous layer was basified to pH 10 by addition of concentrated ammonium hydroxide then washed with ethyl ether (3×25 mL). The combined organic layers were concentrated under vacuum and the residue dissolved in dichloromethane (25 mL). The remaining water was removed in a separatory funnel and the dichloromethane solution dried over sodium sulfate, filtered and concentrated under vacuum. The residual oil was purified by flash column chromatography (5:3 petroleum ether/ethyl acetate together with 2% saturated methanolic ammonia) to give 2c as a waxy solid. mp 115.8–116.9° C. Yield: 0.29 g (54.0%). This compound was converted to the tosylate salt for characterization. mp 182.4–183.8° C.; $[\alpha]_D^{25}$ =39.91° (c 0.451, methanol); $^1$H NMR (CD$_3$OD) 8.7 (d, 2H, J=8.3 Hz), 7.40 (d, 2H, J=8.9 Hz), 7.34 (d, 2H, J=9.0 Hz), 7.22 (d, 2H, J=8.5 Hz), 4.17 (d, 1H, J=6.7 Hz), 3.94 (t, 1H, J=6.3 Hz), 3.67 (s, 3H), 3.34–3.29 (m, 2H), 2.82 (s, 3H), 2.8–2.57 (m, 1H), 2.49–2.38 (m, H), 2.30–2.18 (m, 2H), 2.04–1.92 (m, 2H); $^{13}$C NMR (CD$_3$OD) 8 174.66, 143.65, 141.78, 141.28, 133.99, 130.01, 129.91, 129.85, 127.01, 84.88, 83.39, 53.23, 53.08, 39.71, 35.44, 35.41, 26.36, 26.30, 21.36; Analysis calculated for $C_{23}H_{28}ClNO_5S$: C, 59.28; H, 6.06; N, 3.01. Found: C, 59.34; H, 6.03; N, 2.96.

3α-(4-Methylphenyl)-2β-(3'-methyl-1',2',4'-oxadiazol-5'-yl)tropane tosylate (5d)

A 100 mL two-neck flask was equipped with a stirbar, thermometer with adapter and an addition funnel with nitrogen inlet. The assembly was flame-dried and allowed to cool under nitrogen. The flask was charged with a solution of 4-bromotoluene (3.76 (g, 22 mmol) in 20 mL of anhydrous THF and cooled to 0° C. t-Butyllithium (1.7 M in pentane, 44 mmol, 26 mL) was added dropwise over 15 min. The resulting yellow solution stirred for 20 min, then cooled to −78° C. in a dry ice/acetone bath. The addition funnel was rinsed with 5 mL of anhydrous THF, then charged with a solution of anhydroecgonine oxadiazole (4, 2.05 g, 10.0 mmol) in 10 mL of anhydrous THF. This solution was added to the reaction dropwise, maintaining the temperature below −70° C. A mild exotherm was observed during the addition. The resulting brown solution was stirred at −78° C. for 3.5 h, then quenched at −78° C. by dropwise addition of a 20% solution of trifluoroacetic acid in ethyl ether (25 mL). The reaction was allowed to warm to room temperature, then successively washed with saturated sodium bicarbonate (15 mL) and 1N HCl (2×25 mL). The aqueous phase was washed with ethyl ether (1×25 mL) and the ethereal layers discarded. The aqueous layer was neutralized to pH 10 by addition of concentrated ammonium hydroxide then extracted with dichloromethane (3×50 mL). The organic phase was dried over sodium sulfate, filtered and concentrated under vacuum. The residual oil was purified by flash column chromatography (5:8 ethyl acetate/petroleum ether together with 2% saturated ammonia in methanol) to give 1.97 g (66%) of 5d as a white solid; mp 105.6–107.4° C. Also recovered from the crude product was 0.45 g (15%) of the 2α,3β-isomer. Compound 5d was converted to the tosylate salt for characterization: mp 199.3–200.0° C.; $[\alpha]D^{25}$ =53.50° © 0.415, methanol ; $^1$NMR (CDCl$_3$) d 10.5 (br s, 1H), 7.74 (d, 2H, J=8.1 Hz), 7.15 (d, 2H, J=7.9 Hz), 7.10–6.99 (m, 4H), 4.22 (d, 1H, J=6.6 Hz), 4.19=4.11 (m, 1H), 3.74 (t, 1H, J=7.3 Hz), 3.64 (d, 1H, J=8.1 Hz), 2.91 (s, 3H), 2.61–2.42 (m, 1H), 2.34 (s, 3H), 2.29 (s, 3H), 2.27–2.19 (m, 5H), 2.10–1.84 (m, 3H); $^{13}$C NMR (CDCl$_3$) δ177.62, 167.08, 142.62, 139.64, 136.85, 129.39, 128.60, 126.72, 125.81, 63,98, 62.12, 46.08, 39.62, 35.02, 34.52, 26.49, 25.75, 21.20, 20.81, 11.35; Analysis calculated for $C_{25}H_{31}N_3O_4S$: C, 63.94; H, 6.65; N, 8.95.

3α-(4-Methylphenyl)tropane-2β-carboxylic acid methyl ester tosylate (2d)

A 100 mL r.b. flask equipped with a stirbar and a condenser was charged with nickel(IL) acetate (2.66 g, 10.7 mmol) and methanol (20 mL). A solution of sodium borohydride (0.40 g, 10.7 mmol) in methanol (10 mL) was added dropwise followed by an exothermic reaction. A black colloidal suspension formed immediately. A solution of 5d (0.80 g, 2.7 mmol) in 10 mL of methanol and 0.9 mL of concentrated HCl was added and the resulting mixture heated at reflux for 4 h. The reaction was allowed to cool to room temperature then filtered through celite. The celite was washed with methanol (50 mL) and the filtrate concentrated under vacuum. The residue was diluted with water (10 mL) and poured into ethyl ether (50 ML). The aqueous layer was basified to pH 10 by addition of concentrated ammonium hydroxide then washed with ethyl ether (3×25 mL). The combined organic layers were concentrated under vacuum and the residue dissolved in dichloromethane (25 mL). The remaining water was removed in a separatory funnel and the dichloromethane solution dried over sodium sulfate, filtered and concentrated under vacuum. Flash column chromatography (5:3 petroleum ether/ethyl acetate together with 2% methanolic ammonia) gave 2d as a waxy solid. mp 74.6–76.8° C. Yield: 0.375 g (51%). This compound was characterized as the tosylate salt. mp 174.8–175.4° C.; $[\alpha]D_D^{25}$ −43.14° (c 0.554, methanol); $^1$H NMR (CD$_3$OD) δ7.71 (d, 2H, J=8.2 Hz), 7.27 (d, 2H, J=8.2 Hz), 7.22 (d, 2H, J=8.0 Hz), 7.15 (d, 2H, J=8.1 Hz), 4.13 (d, 1H, J=6.9 Hz), 3.92 (t, 1H, J=6.8 Hz), 3.67 ( s, 3H), 3.38–3.32 (m, 2H), 2.80 (s, 3H), 2.59–2.51 (m, 1H), 2.35 (s, 3H), 2.25 (s, 3H), 2.25–2.12 (m, 3H), 2.01–1.92 (m, 2H); Analysis calculated for $C_{24}H_{31}NO_5S$: C, 64.69; H, 7.01; N, 3.14. Found: C, 64,55, H, 7.04, N, 3.15.

TABLE 1

Chemical Yields and Physical Properties for oxadiazoles 5 and methyl esters 2

| Synthesis Oxadiazole | % Yield | Methyl Ester | % Yield | Molecular Formula[a,b] | Melting Point[a] | [a]D(c) CH$_3$OH |
|---|---|---|---|---|---|---|
| 5a | 85% | 2a | 86% | C$_{20}$H$_{26}$FNO$_8$·0.5H$_2$O[c] | 65° C. (dec) | −34.4° (0.54) |
| 5b | 23%[d] | 2b | 45% | C$_{23}$H$_{28}$INO$_5$S | 204.6–205.3° C. | −38.9° (1.30) |
| 5c | 81% | 2c | 54% | C$_{23}$H$_{28}$ClNO$_5$S | 182.4–183.8° C. | −39.9° (0.45) |
| 5d | 65%[e] | 2d | 51% | C$_{24}$H$_{31}$NO$_5$S | 174.8–175.4° C. | −43.1° (0.55) |
| 5e | 86% | 2e | 60% | C$_{16}$H$_{22}$ClNO$_2$[f] | 178–179° C. | −48.1° (1.38) |

[a]Compounds were characterized as the tosylate salts unless otherwise noted.
[b]C, H, and N analyses were within 0.4% of their theoretical values.
[c]Characterized as the tartrate salt.
[d]The 2α, 3β-isomer was recovered in 20% yield.
[e]The 2α, 3β-isomer was recovered in 15% yield.
[f]Characterized as the HCl salt.

TABLE 2

$^1$H NMR Selected Chemical Shifts and Coupling Constants for the Free Bases of Compounds 2a–d

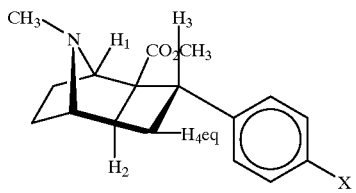

| | | Chemical Shifts (ppm)[a] | | | | | Coupling Constants (Hz) | | |
|---|---|---|---|---|---|---|---|---|---|
| compd | x | 1 | 2 | 3 | 4$_{eq}$ | 4$_{ax}$ | 5 | J$_{1,2}$ | J$_{2,3}$ | J$_{3,4eq}$ |
| 2a | F | 3.41 | 2.65 | 3.63 | 2.37 | 1.32 | 3.09 | 1.8 | 9.7 | 7.9 |
| 2b | I | 3.40 | 2.66 | 3.57 | 2.35 | 1.29 | 3.07 | 1.7 | 9.4 | 7.9 |
| 2c | Cl | 3.41 | 2.65 | 3.59 | 2.35 | 1.30 | 3.08 | 1.7 | 9.4 | 8.0 |
| 2d | CH$_3$ | 3.42 | 2.72 | 3.65 | 2.40 | 1.35 | 3.09 | 1.7 | 9.3 | 2e |
| 2e | H | 3.43 | 2.73 | 3.68 | 2.41 | 1.40 | 3.10 | 1.6 | 9.5 | 8.1 |

[a]Chemical shifts are reported relative to Si(CH$_3$)$_4$ in pyridine-d$_5$ at 500 MHZ.

TABLE 3

Comparison of Transporter Binding Potencies for Stereoisomer of WIN 35, 065-2 Analogs

| | | | IC$_{50}$ (nM)[a] | | | | |
|---|---|---|---|---|---|---|---|
| Compd | X | Isomer | DA [$^3$H]WIN 35,428 | NE [$^3$H]Nisoxetine | 5-HT [$^3$H]Paroxetine | NE/DA Ratio[b] | 5-HT/DA Ratio[b] |
| 6 allococaine[c] | — | — | 6160 ± 900 | — | — | | |
| 7 cocaine[d] | — | — | 89.1 ± 4.8 | 3,298 ± 293 | 1,045 ± 89 | | |
| 1a[e,f] | F | 2β, 3β | 14 ± 1.4 | 835 ± 45 | 810 ± 59 | 60 | 58 |
| 2a | F | 2β, 3α | 21 ± 0.57 | 1,230 ± 91 | 5,060 ± 485 | 59 | 241 |
| 1b[e] | I | 2β, 3β | 1.26 ± 0.04 | 36 ± 2.7 | 4.21 ± 0.3 | 29 | 3.3 |
| 2b | I | 2β, 3α | 2.85 ± 0.16 | 52.4 ± 4.9 | 64.9 ± 1.97 | 18 | 23 |
| 1c[e] | Cl | 2β, 3β | 1.12 ± 0.1 | 37 ± 2.1 | 44.5 ± 1.3 | 33 | 40 |
| 2c | Cl | 2β, 3α | 2.4 ± 0.2 | 60.1 ± 2.4 | 998 ± 120 | 25 | 415 |
| 1d[e] | CH$_3$ | 2β, 3β | 1.71 ± 0.31 | 60 ± 0.53 | 240 ± 27 | 35 | 140 |
| 2d | CH$_3$ | 2β, 3α | 10.2 ± 0.8 | 275 ± 24 | 4,250 ± 422 | 27 | 417 |
| 1e[g,h] | H | 2β, 3β | 23 ± 5 | 920 ± 73 | 2,000 ± 64 | 40 | 87 |
| 2e | H | 2β, 3α | 101 ± 16 | 2,080 ± 528 | 5,700 ± 721 | 21 | 57 |
| 8e | H | 2β, 3β | 100 | 3830 | 7880 | 38 | 79 |
| 9e | H | 2β, 3α | 167 | 40,600 | 6990 | 243 | 42 |
| 8a | F | 2β, 3β | † | † | † | — | — |

TABLE 3-continued

Comparison of Transporter Binding Potencies for Stereoisomer of WIN 35, 065-2 Analogs

| | | | IC$_{50}$ (nM)[a] | | | | |
|---|---|---|---|---|---|---|---|
| Compd | X | Isomer | DA [³H]WIN 35,428 | NE [³H]Nisoxetine | 5-HT [³H]Paroxetine | NE/DA Ratio[b] | 5-HT/DA Ratio[b] |
| 9a | F | 2β, 3α | † | † | † | — | — |
| 8c | Cl | 2β, 3β | 4.0 | 2580 | 363 | 645 | 91 |
| 9c | Cl | 2β, 3α | 3.5 | 2178 | 278 | 622 | 79 |
| 9b | I | 2β, 3α | 3.2 | 6.5 | 14.9 | 2.0 | 4.7 |
| 9d | CH$_3$ | 2β, 3α | 5.42 | 9970 | 485 | 1839 | 89 |

[a]Data are mean ± standard error of three or four experiments performed in triplicate.
[b]Ratios of IC$_{50}$ values.
[c]IC$_{50}$ values taken from reference 10.
[d]IC$_{50}$ values taken from literature.
[e]IC$_{50}$ values from literature
[f]This compound is WIN-35,428.
[g]This compound is WIN-35,065-2.
[h]IC$_{50}$ values taken from literature.
† Data not available Scheme 1

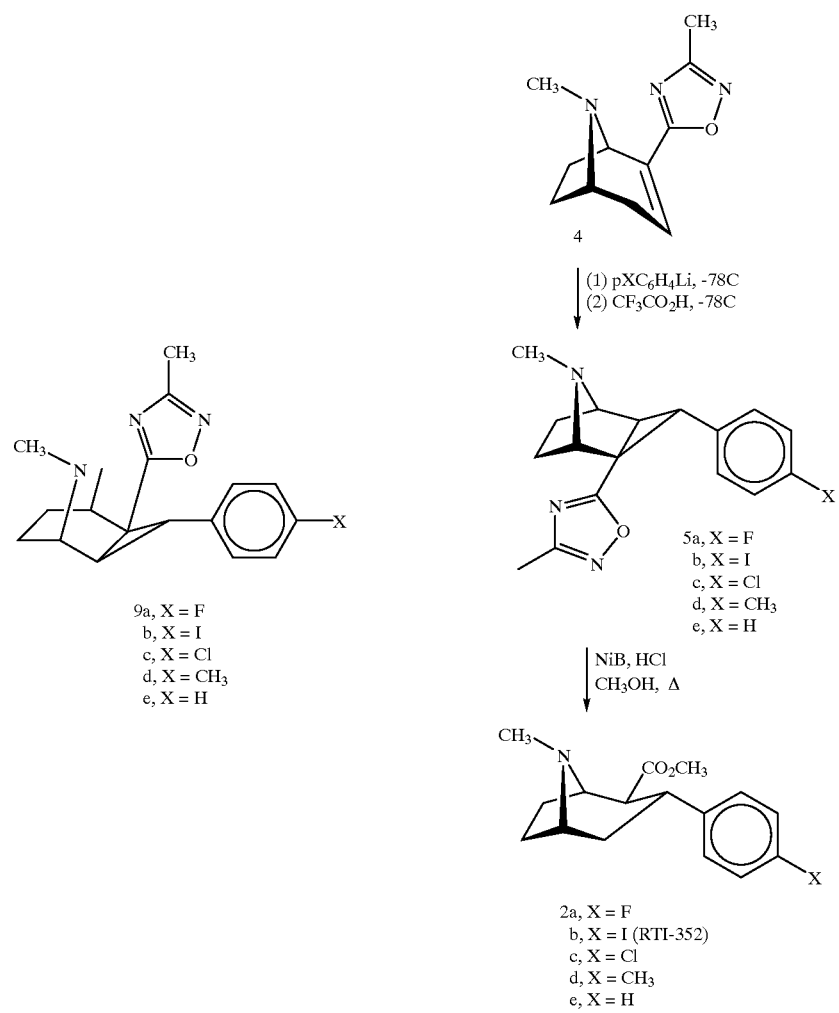

Scheme 2

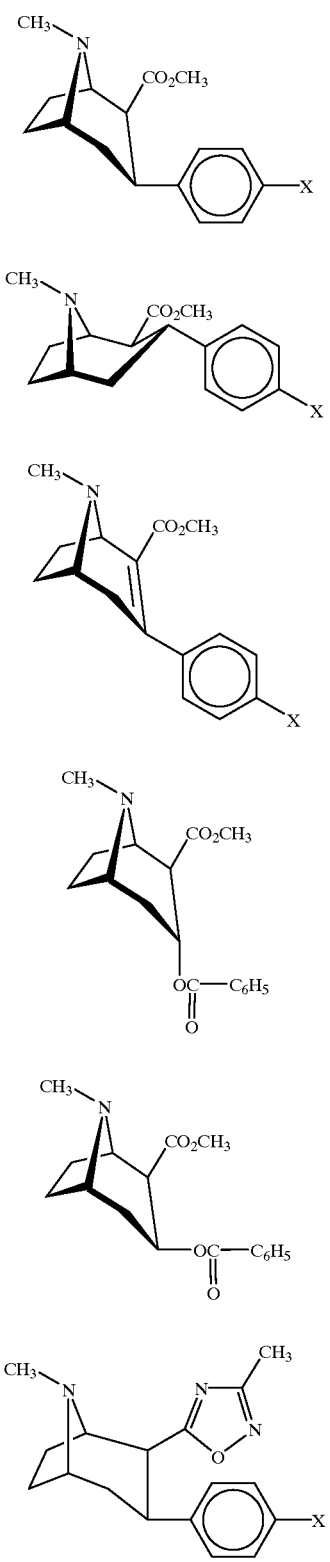

Scheme 3

What is claimed as new and desired to be secured by Letters Patent of the United States is:

1. A 3α-(substituted phenyl)tropane-2β-carboxylic acid methyl ester of formula 2:

2 wherein X is selected from the group consisting of F, I, Cl, $CH_3$ and H.

2. The compound of claim 1, wherein X is radioactive iodine.

3. A method of selectively binding dopamine transporter in a patient in need of same, comprising administering an effective amount of a pharmaceutical preparation of the compound of claims 1 or 2 to said patient.

* * * * *

UNITED STATES PATENT AND TRADEMARK OFFICE
CERTIFICATE OF CORRECTION

PATENT NO.    : 6,358,492 B1
DATED         : March 19, 2002
INVENTOR(S)   : Michael J. Kuhar et al.

It is certified that error appears in the above-identified patent and that said Letters Patent is hereby corrected as shown below:

<u>Title page,</u>
Item [57], ABSTRACT,
Lines 11-13, should read:
-- 3β-(substituted phenyl)tropanes will result in greater selectivity for dopamine transporters and a more rapid achievement of apparent equilibrium. --.

<u>Column 8,</u>
Line 18, "methanol; $^1$NMR (CDCl$_3$) d 10.5" should read -- methanol; $^1$H NMR (CDCl$_3$) d 10.5 --.

Signed and Sealed this

Twenty-seventh Day of August, 2002

*Attest:*

*Attesting Officer*

JAMES E. ROGAN
*Director of the United States Patent and Trademark Office*